US009297799B2

(12) United States Patent
Ohnishi et al.

(10) Patent No.: US 9,297,799 B2
(45) Date of Patent: Mar. 29, 2016

(54) METHOD FOR MEASURING PROTOZOAN OOCYST AND DETECTING REAGENT

(75) Inventors: Noriyuki Ohnishi, Ichihara (JP); Hirotaka Furukawa, Rye, NY (US); Hideyuki Hata, Ichihara (JP); Kageaki Matsui, Ichihara (JP); Takako Nogami, Tokyo (JP); Hideo Nishizawa, Tokyo (JP); Akihiko Kondo, Hyogo (JP)

(73) Assignees: NATIONAL UNIVERSITY CORPORATION KOBE UNIVERSITY, Hyogo (JP); JNC CORPORATION, Tokyo (JP)

( * ) Notice: Subject to any disclaimer, the term of this patent is extended or adjusted under 35 U.S.C. 154(b) by 1394 days.

(21) Appl. No.: 11/813,563

(22) PCT Filed: Jan. 11, 2006

(86) PCT No.: PCT/JP2006/300205

§ 371 (c)(1),
(2), (4) Date: Oct. 10, 2007

(87) PCT Pub. No.: WO2006/075612

PCT Pub. Date: Jul. 20, 2006

(65) Prior Publication Data

US 2008/0199884 A1 Aug. 21, 2008

(30) Foreign Application Priority Data

Jan. 11, 2005 (JP) ................................ 2005-004426

(51) Int. Cl.

*G01N 33/553* (2006.01)
*G01N 33/543* (2006.01)
*G01N 33/569* (2006.01)

(52) U.S. Cl.

CPC .... *G01N 33/54326* (2013.01); *G01N 33/56905* (2013.01)

(58) Field of Classification Search

CPC .................. G01N 33/54326; G01N 33/56905
See application file for complete search history.

(56) References Cited

U.S. PATENT DOCUMENTS

| | | | |
|---|---|---|---|
| 2003/0165962 A1 | 9/2003 | Furukawa et al. | |
| 2003/0175826 A1 | 9/2003 | Furukawa et al. | |
| 2005/0158782 A1 | 7/2005 | Furukawa et al. | |

FOREIGN PATENT DOCUMENTS

| | | |
|---|---|---|
| EP | 1316599 B1 * | 8/2001 |
| EP | 1312671 | 5/2003 |
| JP | 11-243953 | 9/1999 |
| WO | 02/16528 | 2/2002 |
| WO | 02/16571 | 2/2002 |

OTHER PUBLICATIONS

Hsu et al (Biotechnol. Prog. 17:1114-1118, 2001).*
Measure against Cryptosporidium in Tap Water, supervised by Ministry of Health and Welfare, Life Hygiene Bureau, Water Environment Division, Water Maintenance Department, published by K.K. Gyousei (Dec. 1999), pp. 1-2.
English Language Abstract of JP 11-243953.
Deng et al. "Immunomagnetic Separation° of *Cryptosporidium parvum* Oocysts using MACS MicroBeads and High Gradient Separation Columns" Journal of Microbiological Methods, vol. 40 (2000), pp. 11-17.

* cited by examiner

*Primary Examiner* — Patricia Duffy
(74) *Attorney, Agent, or Firm* — Greenblum Bernstein, P.L.C.

(57) ABSTRACT

The present invention provides a method for measuring oocyst of protozoa, such as *Cryptosporidium*, in an environment sample with high sensitivity at low cost within a short period of time; and a detecting reagent for use therein. Magnetic fine particles of 5 to 500 nm particle diameter having, immobilized thereto, binding factors for specific recognition of oocyst are added to an analyte containing a protozoan oocyst to form oocyst/binding factor/magnetic fine particle complexes by using a binding reaction to the oocyst, the formed complexes are recovered by a magnetic separation, and the protozoan oocysts contained in the complexes are assayed. Further, there is provided, for conducting the above method, a reagent for detecting protozoan oocysts comprising magnetic fine particles of 5 to 500 nm particle diameter having, immobilized thereto, antibodies against oocysts or binding factors for recognizing the antibodies.

8 Claims, 3 Drawing Sheets

B

METHOD FOR MEASURING PROTOZOAN OOCYST AND DETECTING REAGENT

TECHNICAL FIELD

The present invention relates to a method for measuring protozoan oocyst and a reagent for detecting the same, capable of inexpensively and conveniently detecting the presence of a protozoan oocyst in various environments such as raw water for tap water, waste water, sewage, natural water and soil.

BACKGROUND ART

Tap water, groundwater, stream water, and the like are ingested as drinking water and also there is a possibility that they are unconsciously taken up from mouth, so that it is necessary to pay attention to their treatment in view of good hygiene. In addition to bacteria and suspended particulates, attention has been recently paid to protozoa such as *Cryptosporidium*.

*Cryptosporidium* is a digestive tract-parasitic protozoan which is parasitic on mucous membranes of stomach and intestinal tracts to cause diarrhea. *Cryptosporidium* proliferates with repeating an asexual reproduction term and a sexual reproduction term and oocysts generated from the result of sexual reproduction are discharged into feces of parasitic hosts. Since the oocyst is stable and maintains activity for a long period of time, contamination of stream water and groundwater with oocysts discharged into for some reasons into drinking water may invite a situation that the oocyst infects human. In an infection example which occurred in Ogose-cho, Saitama-prefecture in 1996, a sewage-treatment plant exists at the upper stream of a river of raw water for tap water and thus oocyst as a primary infection source is considered to enter into tap water through a drinking-water treatment plant using the stream water as water source. Furthermore, discharged water from lavatories used by patients developing symptoms had been treated as sewage and again flew into the river and the stream water was utilized as a water source for tap water, so that infection was extended successively and finally a half of citizens were infected.

Oocyst of *Cryptosporidium* has an extremely strong resistance against disinfection by chlorine and treatment with ozone and thus it is impossible to completely annihilate the oocysts in water by usual water-purifying treatment. Therefore, in order to prevent infection with *Cryptosporidium* via water, it is necessary to assay a minute amount of oocysts in a sample in high accuracy together with sufficient removal or disinfection of the pathogenic protozoan.

Ministry of Health, Labor and Welfare has determined a guideline for tentative measure on preventive action and emergency action against these chlorine-resistant microorganisms (e.g., see Non-Patent Document 1). In the document, various methods for measuring *Cryptosporidium* are listed, including descriptions of an operating method comprising three steps: a "concentration step" where a collected sample is concentrated by one of the methods such as suction filtration, pressure filtration, cartridge filter method, or centrifugal precipitation, a "separation/purification step" where protozoan oocysts are separated from other suspending substances and purified by a method such as density-gradient centrifugal precipitation or immunological magnetic particle method (immunological magnetic bead method), and a subsequent "staining/microscopic inspection step" where the protozoan oocysts are immunologically stained and measured on a microscope; or an operating method comprising the above "concentration step" and "staining/microscopic inspection step".

However, in the case that oocysts are separated from an environmental sample using a centrifugal means, specific gravity of *Cryptosporidium* is close to specific gravities of water and other contaminants and hence oocysts of *Cryptosporidium* present in the environmental sample cannot be completely recovered by conducting common low-speed centrifugal separation alone.

Moreover, in the guideline for tentative measure of Ministry of Health, Labor and Welfare, an immunological magnetic bead method is recommended as the above "separation/purification step" in the detection and measurement of oocysts of *Cryptosporidium*. This method is a method wherein immunological magnetic beads of 5 to 6 μm diameter are added to a sample subjected to the concentration step to effect an immune reaction and the oocysts bound onto the beads are magnetically recovered together with the beads. It may be convenient to observe the recovered oocysts directly through immunological fluorescent staining but actually, it is impossible to discriminate the oocysts because the immunological magnetic beads exhibit autofluorescence and also resemble the oocysts in size. Therefore, there is required a step of dissociating the oocysts from the magnetic beads having the oocysts bound thereto with hydrochloric acid. After the dissociation, a portion of the acid dissociation liquid containing the oocysts is placed on a glass slide and then neutralized with an alkali. After the solution of the preparation is air-dried, it is washed with methanol and then the oocysts are stained with fluorescent antibodies. The staining takes 30 minutes. Furthermore, in order to remove unbound fluorescent antibodies, washing is conducted but full attention should be paid so as not to wash out the oocysts from the preparation. Moreover, since a high-concentration salt is precipitated by the neutralization, the staining is not homogeneously effected and it is difficult to discriminate fluorescent oocysts from background in some cases. Also, in the operation for dissociation, all the oocysts are not always dissociated and some oocysts may remain on the magnetic beads, so that the recovery ratio is also problematic. Thus, the conventional method with the micron-size magnetic beads has defects that the steps are tedious and complex, a lot of skills are required for fluorescent staining, and also the recovery ratio of oocysts is insufficient.

Particularly, in the assay of tap water, since it is necessary to find one or two oocysts in a large amount of water, it is difficult even for those who attend skill-training to decide whether a substance emitting fluorescence belongs to *Cryptosporidium* or not and there are even confused cases induced by reports of mistaken detection, so that various problems remain on the method for detecting *Cryptosporidium* and thus water quality criteria therefor has not yet been defined. The reasons for requiring considerable skill in this assay method are that it takes a lot of time to concentrate *Cryptosporidium* from an analyte and that it requires the skill to discriminate *Cryptosporidium* oocysts under a fluorescent microscope.

As another staining/microscopic inspection step, anti-acid staining has been also developed but non-specific reaction with substances other than oocysts occurs remarkably in this method and thus there is a problem that the judgment of oocyst is difficult for a person who is not considerably skilled specialist.

As the other method for detecting *Cryptosporidium*, there has been known a method for detecting a specific DNA sequence of *Cryptosporidium* using a PCR process (e.g., see Patent Document 1). The method is a method wherein *Cryptosporidium* recovered by centrifugation is treated according to conventional procedures such as proteolytic treatment using proteinase K, phenol-chloroform treatment, and ethanol precipitation to recover DNA and then a sequence specific to *Cryptosporidium* is amplified by a PCR process to detect the presence of *Cryptosporidium.*

However, this method employs a thermal cycler for amplifying DNA and a primer having a specific base sequence and hence is by no means an inexpensive and convenient method.

Furthermore, in both of the method using a specific antibody and a method of recognizing a specific DNA sequence by a PCR process, centrifugation is used at the time when *Cryptosporidium* is recovered. However, since specific gravities of oocysts and sporozoites of *Cryptosporidium* are near to 1, there is a large loss part impossible to recover by general low-speed centrifugation and hence there is a problem that *Cryptosporidium* present in a sample cannot be sufficiently detected.

Non-Patent Document 1: Measure against *Cryptosporidium* in Tap Water, supervised by Ministry of Health and Welfare, Life Hygiene Bureau, Water Environment Division, Water Maintenance Department, published by K. K. Gyousei (December, 1999), pp. 1-2.

Patent Document 1: JP-A-11-243953

DISCLOSURE OF THE INVENTION

Problems that the Invention is to Solve

Accordingly, an object of the invention is to provide a method of measuring oocyst of protozoa, such as *Cryptosporidium*, in an environment sample with high sensitivity at low cost within a short period of time. The invention provides a convenient and highly sensitive method for measuring protozoan oocyst and a detecting reagent for use therein.

Means for Solving the Problems

As a result of the extensive studies, the present inventors have found that the above problems are solved by the use of magnetic fine particles of 5 to 500 nm particle diameter (hereinafter also referred to as “magnetic nanoparticle”), which are different from micron-size magnetic beads for use in the conventional immunological magnetic beads method, and thus have accomplished the invention based on the findings.

Namely, the above object can be achieved by the following constitutions.

(1) A method for measuring protozoan oocysts, which comprises:

adding magnetic fine particles of 5 to 500 nm particle diameter, which have a binding factor for specifically recognizing protozoan oocysts immobilized thereto, to an analyte containing protozoan oocysts to form complexes of the oocysts with the magnetic fine particles through the binding factor;

recovering the thus formed oocyst/binding factor/magnetic fine particle complexes by a magnetic separation; and counting the number of oocysts.

(2) The method for measuring protozoan oocysts according to the above (1), wherein the binding factor is an antibody against oocyst (hereinafter referred to as “antioocyst antibody”).

(3) The method for measuring protozoan oocysts according to the above (1) or (2), wherein the oocyst/binding factor/magnetic fine particle complexes are oocyst/antioocyst antibody/magnetic fine particle complexes formed by adding magnetic fine particles having the antioocyst antibody immobilized thereto to the analyte.

(4) The method for measuring protozoan oocysts according to the above (1), wherein the binding factor comprises the antioocyst antibody and a binding factor component specifically recognizing the antibody (hereinafter referred to as “antioocyst antibody-binding factor component”).

(5) The method for measuring protozoan oocysts according to the above (1), wherein the oocyst/binding factor/magnetic fine particle complexes are oocyst/antioocyst antibody/antioocyst antibody-binding factor component/magnetic fine particle complexes, which are formed by adding antibodies against oocyst to an analyte to form oocyst/antioocyst antibody complexes, and subsequently adding magnetic fine particles having the antioocyst antibody-binding factor component against the antibody immobilized thereto.

(6) The method for measuring protozoan oocysts according to any one of the above (1) to (5), wherein the magnetic fine particles are labeled beforehand.

(7) The method for measuring protozoan oocysts according to any one of the above (1) to (5), wherein the formed oocyst/binding factor/magnetic fine particle complex is further labeled.

(8) The method for measuring protozoan oocysts according to the above (6) or (7), wherein the labeling is a fluorescent labeling.

(9) The method for measuring protozoan oocysts according to any one of the above (1) to (8), wherein the magnetic fine particles are magnetic fine particles having stimuli-responsive polymers immobilized thereto.

(10) The method for measuring protozoan oocysts according to any one of the above (1) to (9), wherein the protozoan is a protozoan belonging to genus *Cryptosporidium.*

(11) The method for measuring protozoan oocysts according to any one of the above (1) to (10), wherein the analyte contains water as a solvent.

(12) A reagent for detecting protozoan oocysts in an analyte, which comprises magnetic fine particles of 5 to 500 nm particle diameter having antioocyst antibodies or antioocyst antibody-binding factor components immobilized thereto.

(13) The reagent for detecting protozoan oocysts according to the above (12), wherein the above magnetic fine particles are magnetic fine particles having stimuli-responsive polymers immobilized thereto.

Advantage of the Invention

According to the invention, there can be obtained a method for measuring protozoan oocyst and a reagent for detecting protozoan oocyst, which allows detection of protozoan oocyst conveniently and rapidly in high accuracy without requiring skilled specialists.

BRIEF DESCRIPTION OF THE DRAWINGS

FIG. 1A is a schematic drawing of an immunocomplex (*Cryptosporidium* oocyst/anti*Cryptosporidium* oocyst antibody/magnetic bead complex) using a conventional magnetic bead method. FIG. 1B is a schematic drawing of a *Cryptosporidium* oocyst/anti*Cryptosporidium* oocyst antibody/anti*Cryptosporidium* oocyst antibody binding factor component/stimuli-responsive polymer/magnetic nanoparticle complex using magnetic nanoparticles according to the invention.

BEST MODE FOR CARRYING OUT THE INVENTION

In the invention, to an analyte containing protozoan oocyst is added magnetic fine particles of 5 to 500 nm particle diameter having, immobilized thereto, binding factors for specific recognition of the oocysts, thereby oocyst/binding factor/magnetic nanoparticle complexes being formed. Thus, owing to the fine particle property, the binding reaction with the oocyst extremely rapidly proceeds and also no autofluorescence is observed on the magnetic nanoparticles, so that there becomes unnecessary a step of dissociating magnetic particle from the oocysts with hydrochloric acid which is conventionally an essential step. Namely, the complex can be recovered and subjected to the next detection step in the state of the "oocyst/binding factor/magnetic nanoparticle complex" wherein magnetic nanoparticles and oocysts are bound through the binding factor, and hence rapidness and recovery ratio are remarkably improved.

Figure 1:
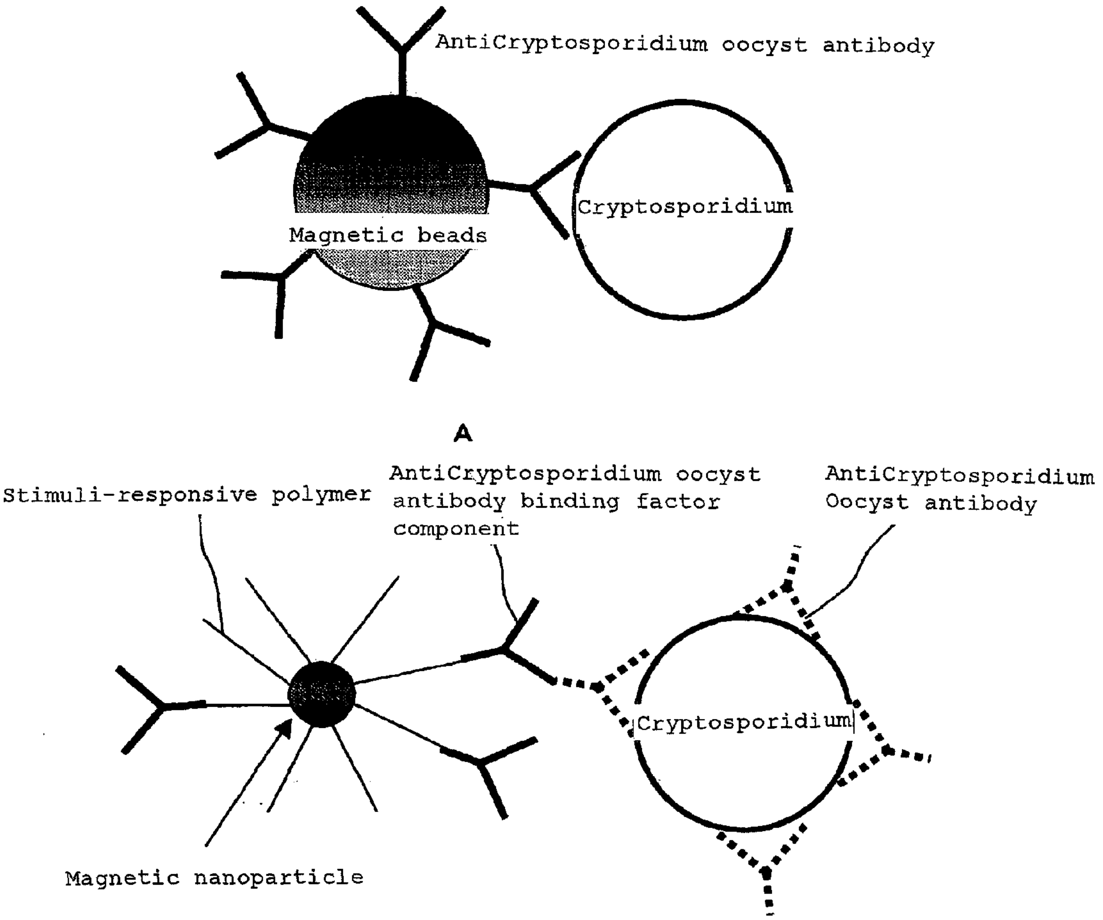
FIG. 1 is a schematic drawing of an immunocomplex.

FIG. 1A schematically represents a *Cryptosporidium* oocyst/anti*Cryptosporidium* oocyst antibody/magnetic bead complex by means of an immunological magnetic beads having, immobilized thereto, an antibody against oocyst of protozoa belonging to Genus *Cryptosporidium* (hereinafter referred to as "anti*Cryptosporidium* oocyst antibody").

FIG. 1B schematically represents a complex of magnetic nanoparticle having, immobilized thereto, a stimuli-responsive polymer bound to an anti*cryptosporidium* oocyst antibody binding factor component with an anti*cryptosporidium* oocyst antibody-*Cryptosporidium* oocyst complex.

The conventional immunological micron-size magnetic beads have aforementioned defects. To the contrary, with regard to the magnetic nanoparticles for use in the invention, sufficient dispersibility is obtained owing to the remarkably small particle diameter and hence the recovery ratio of oocysts existing in a minute amount is improved. The improvement of dispersibility results in a rapid binding reaction, which leads to shortening of the step. One hour of the reaction time required in the case of the conventional micron-size magnetic beads is shortened to several tens seconds in the case of the magnetic nanoparticles for use in the invention. Particularly, in the magnetic nanoparticles having, immobilized thereto, the stimuli-responsive polymers described in FIG. 1B, since the aggregate is formed depending on change in temperature or pH, it is easy to recover the dispersed magnetic fine particles. Namely, when the dispersed magnetic nanoparticles are aggregated by changing temperature or pH, the particles can be easily recovered by setting a magnetic plate or the like. Therefore, centrifugation or the like is not necessary. In addition, since the magnetic nanoparticles and the stimuli-responsive polymers exhibit no autofluorescence, it is possible to enter the next detection (labeling/microscopic inspection) step after the recovering operation without separating the magnetic beads from oocysts. The easiness of dispersion/recovery simplifies the staining step. Specifically, a buffer solution and fluorescent antibodies are added to the recovered magnetic nanoparticles and pipetting is continued in a dispersed state for dozens of seconds. Then, the particles are converted into an aggregated state and recovered with a magnetic plate, and then the resulting supernatant is discarded. A buffer solution is further added thereto and pipetting is further continued in a dispersed state for dozens of seconds. Then, the particles are converted into an aggregated state and recovered with a magnetic plate, and then the resulting supernatant is discarded, followed by washing. The operations are further repeated twice to obtain a highly purified sample for observation.

Moreover, in the invention, a binding method for formation of the complex of the magnetic nanoparticles with oocysts, a timing and site for binding them are arbitrary. For example, immunocomplexes may be formed by preparing magnetic nanoparticles having an antibody against oocyst immobilized thereto beforehand and adding the particles to an analyte containing oocysts. Alternatively, an oocyst/antioocyst antibody/antioocyst antibody binding factor component/magnetic fine particle complexes may be formed by adding an antibody against oocyst to an analyte containing oocysts to form an oocyst/antioocyst antibody complex and adding magnetic nanoparticles having, immobilized thereto, a binding factor recognizing the antioocyst antibody into the sample. Also, biotin, avidin, a biotinylated antibody, and the like can be freely utilized. A complex may be directly formed between antioocyst antibody and magnetic nanoparticles or a complex may be formed indirectly through biotin, avidin, biotinylated antibody, or the like.

Moreover, in the invention, a complex labeled in one step can be formed by forming a complex with oocyst using magnetic nanoparticles labeled beforehand. In this case, also, shortening of the step and improvement of accuracy are achieved.

Furthermore, when magnetic nanoparticles having, immobilized thereto, stimuli-responsive polymers containing a binding factor bound thereto are used as magnetic nanoparticles, the oocysttimuli-responsive polymer immobilized magnetic nanoparticle complex is easily aggregated by imparting the corresponding stimulation, so that recovery of the complex is facilitated and thus the case is preferable.

The following will describe the invention further in detail.

First, there is described an antibody against protozoan oocyst or magnetic nanoparticle having, immobilized thereto, a binding factor component specifically recognizing the antibody.

The material for the magnetic nanoparticles for use in the invention may be an organic substance or inorganic substance so far as it is a substance exhibiting magnetism at ordinary temperature. The substance exhibiting magnetism is not particularly limited but specifically includes nickel oxide particles, ferrite particles, magnetite particles, maghemite particles, cobalt iron oxide, barium ferrite, carbon steel, tungsten steel, KS steel, particles of rare-earth cobalt magnets, hematite particles, and the like.

The particle diameter of the magnetic nanoparticles is in the range of 5 to 500 nm, preferably in the range of 20 to 150 nm. When the particle diameter of the magnetic nanoparticles is adjusted to this range, surface area per unit volume of the magnetic nanoparticles can be increased and hence sensitivity toward an antigen (oocyst) in an immunological magnetic bead method can be remarkably improved. Moreover, shortening of the time for the binding reaction can be also achieved. When the particle size of the magnetic nanoparticles is less than 5 nm, the time for magnetic separation is necessary and it requires a lot of time. When the size exceeds 500 nm, there is a risk of decrease in recognizing ability toward oocyst.

The method for preparing the magnetic nanoparticle for use in the invention is described with reference to the case using magnetite as an example. Magnetic magnetite fine particles having a particle diameter of several tens nm can be obtained by converting magnetite into double micelles using sodium oleate and sodium dodecylbenzenesulfonate and dispersing the micelles into an aqueous solution. This method is a method described in Biocatalysis, 1991, Vol. 5, pp. 61-69.

The binding factor to be immobilized to the magnetic nanoparticles is not particularly limited so far as it is a molecule having a specific binding ability toward protozoan oocyst and having a function capable of binding oocyst to the magnetic nanoparticles to form a complex. The factor may be constituted by a single component or may be constituted by plurality of binding factor components. Moreover, an antibody or the like may be used as the binding factor. In the invention the complex of magnetic nanoparticles containing an antibody such as antioocyst antibody is sometimes referred to as an immunological magnetic nanoparticles, and the complex of oocysts and the immunological magnetic nanoparticles is sometimes referred to as an immunocomplex.

Moreover, the method for immobilization thereof is not particularly restrictive and conventionally known methods may be used. As the method for immobilizing the binding factor on the magnetic nanoparticles, in the case of using an antibody, for example, there may be mentioned a method of immobilizing the antibody onto the nanoparticle surface by a condensation or addition reaction with a functional group (e.g., carboxyl group, amino group, or epoxy group) immobilized onto the surface of the nanoparticles beforehand utilizing an amino acid residue (e.g., amino group, carboxyl group, or the like) existing on the surface of the binding factor.

Furthermore, as a biochemical procedure, there may be mentioned a method of immobilizing biotin to the surface layer of the nanoparticles beforehand, binding avidin having a specific binding ability toward biotin, further forming a biotinylated antibody using a commercially available biotinylation kit, and subsequently immobilizing an antibody onto the surface of the nanoparticles utilizing an avidin-biotin bond formed in an aqueous solution.

As specific forms mediating the bond between the magnetic nanoparticles and oocysts, there may be, for example, mentioned biotin and avidin, an antigen and an antibody, a polynucleotide and a polynucleotide having a base sequence complementary to the polynucleotide, an enzyme (active site) and a substrate, an enzyme (active site) and a product, an enzyme (active site) and a competitive inhibitor, an enzyme (coenzyme binding site) and a coenzyme, an enzyme (coenzyme binding site) and a triazine pigment, an Fc site and protein A, an Fc site and protein G, lectin and a sugar, a hormone receptor and a hormone, a DNA and a DNA binding protein, heparin and fibronectin, and heparin and laminin.

In the invention, as the magnetic nanoparticles, it is preferred to use those having a stimuli-responsive polymer immobilized thereto. Thereby, the magnetic nanoparticles having the above stimuli-responsive polymers immobilized thereto can be precipitated and aggregated by imparting the corresponding stimulation and thus recovery of the magnetic nanoparticles by means of a magnet can be more efficiently conducted.

The stimuli-responsive polymer herein means a polymer having a property of precipitating and aggregating the polymer in a solvent containing the polymer in response to stimulation such as temperature, pH, light, magnetic field, or electricity. When the above stimuli-responsive polymer is immobilized to the magnetic nanoparticle, after oocyst and immunological magnetic nanoparticle form an immunocomplex, the immunocomplex is aggregated by imparting stimulation to the solvent containing the immunocomplex, so that it can be easily magnetically separated (recovered). Any of the conventionally known stimuli-responsive polymers can be used.

In the invention, as preferred stimuli-responsive polymers, there may be, for example, mentioned a pH responsive polymer wherein a physical property (solubility toward a solvent, a form, or the like) responds to change in pH, a light responsive polymer wherein a physical property responds to change in wavelength of light, and a heat responsive polymer wherein a physical property responds to change in temperature. Particularly preferred is a heat responsive polymer. The heat responsive polymer means a polymer which reversibly repeats aggregation and dissolution in an aqueous solution upon temperature change. As the heat responsive polymer, there are known a polymer having lower critical solution temperature (LCST) and a polymer having upper critical solution temperature (UCST). Specifically, poly-N-isopropylacrylamide is known as a polymer exhibiting LCST in an aqueous solution and its phase transition temperature is 32° C. A copolymer of acrylamide and N-acetylacrylamide or the like is known as a polymer exhibiting UCST in an aqueous solution and its phase transition temperature can be varied depending on the ratios of individual monomer components.

As the heat responsive magnetic nanoparticles, there may be mentioned magnetic particles described in International Publication WO02/16528 pamphlet, International Publication WO02/16571 pamphlet, and the like.

The following will describe the measuring method of the invention.

In the invention, the "environmental sample" means raw water for tap water, soil, waste water, sewage, pool water, feces, or the like. The environmental sample may be subjected to a concentration step according to need and thus may be the analyte for subjecting to the purification/separation step of the invention.

In the invention, the "oocyst" means one wherein zygote is enwrapped with a membrane. The zygote is divided inside the oocyst to form sporozoite having infectivity. An oocyst has a characteristic that it is extremely resistant to environmental change, such as dryness and chemicals, owing to the presence of the shell.

In the invention, in the recovery of protozoan oocyst by the conventional immunological magnetic bead method, it becomes possible to recover protozoan oocyst in higher sensitivity by the use of magnetic nanoparticles instead of the conventional micron-size magnetic beads.

For example, in the case of using magnetic nanoparticles having UCST polymers bound thereto, by adding into an analyst the magnetic nanoparticles having an antibody against oocyst immobilized thereto and stirring the whole with pipetting operation or the like for dozens of seconds (preferably 20 to 60 seconds), it is possible to form an "immunocomplex" wherein oocysts and magnetic nanoparticles are bound through the antibody. As compared with the reaction time required in the conventional micron-size immunological magnetic bead method. i.e., 1 hour, the reaction time can be remarkably shortened.

Thereafter, the immunocomplex is recovered by magnetic separation. As the magnetic separation method, conventionally known methods can be employed.

The magnetic nanoparticles having stimuli-responsive polymers according to the invention immobilized thereto repeat aggregation/dissolution upon change in heat, thermal shock, or pH. Therefore, when the above magnetic nanoparticles added to the reaction solution are aggregated beforehand by change in heat or pH, the particles can be easily separated with a magnet. Owing to small particle diameter, reactivity for recognition binding is high and separation is easy, so that a magnetic column or the like is not necessary. Therefore, the stimuli-responsive polymer-immobilized magnetic fine particles (stimuli-responsive magnetic nanoparticle) of 5 to 500 nm particle diameter having an antibody against protozoan oocyst immobilized thereto are effective as a detecting reagent.

In the invention, particularly, by the use of heat responsive magnetic nanoparticles which reversibly repeat dissolution/aggregation in an aqueous solution upon slight temperature change, *Cryptosporidium* oocysts in an environmental sample as an analyte can be efficiently recovered. This is because the above magnetic nanoparticles show excellent dispersibility in an appropriate temperature range. At the same time, since the above heat responsive magnetic nanoparticles are aggregated upon temperature change, recovery thereof is easy.

For example, in the case of heat responsive magnetic nanoparticles obtained by immobilization of an LCST polymer, the heat responsive magnetic nanoparticles can be aggregated with heating operation. To the contrary, in the case of heat responsive magnetic nanoparticles obtained by immobilization of UCST polymers, the heat responsive magnetic nanoparticles can be aggregated with cooling operation. A washing operation is facilitated by magnetic separation of the aggregate through prompt action of a magnet and discarding supernatant. Furthermore, the aggregate can be sufficiently dispersed with cooling in the case of heat responsive magnetic nanoparticles obtained by immobilization of LCST polymers and with heating in the case of heat responsive magnetic nanoparticles obtained by immobilization of UCST polymers, so that removal of non-specifically bound matter and removal of unbound antibody for fluorescent staining can be efficiently conducted. Each of the steps for dispersion/aggregation takes only dozens of seconds.

Then, the number of the oocyst in the analyte is measured by conducting a detecting step of the oocyst. In the invention, the oocyst to which the above magnetic nanoparticles are bound can be subjected to the next detection step as they are (without elution/dissociation of the magnetic fine particles).

In the invention, the above immunocomplex is preferably labeled by a conventionally known method and thereby, the oocyst can be easily detected by microscopic inspection. Moreover, in the invention, as mentioned above, since it is not necessary to dissociate magnetic nanoparticles, a "labeled complex" can be obtained in one stage by the use of magnetic nanoparticles labeled beforehand.

The detection step using a label usable in the invention is not particularly limited so far as it includes a step of labeling and measuring a complex formed by reacting the oocyst and the magnetic nanoparticles and a method usually used in the art can be suitably applied. For example, any of a direct method, an indirect method, a homogeneous method, a heterogeneous method, and the like in immunoassay may be used. Moreover, there may be employed any of radioimmunoassay using RI, enzyme immunoassay using an enzyme such as alkaline phosphatase or peroxidase, fluorescent immunoassay using a fluorescent substance, as the label for use in detection of the complex.

Preferred is a method of labeling with a fluorescent substance and fluorescent substances commonly used in the immunofluorescence method may be suitably used. For example, there may be mentioned fluorescein, rhodamine, sulforhodamine 101, lucifer yellow, acridine, riboflavin, and the like. Preferred is fluorescein.

It is desired that the number of the oocysts of *Cryptosporidium* existing in the environmental sample is detected at a unit of several oocysts. Drinking water such as raw water for tap water should not be contaminated with any oocyst of *Cryptosporidium*. In an environmental sample, particularly a sample relating to tap water or drinking water, it is required to detect only 1 or several oocysts. In the above observation method, it is possible to correctly and clearly count the number of oocyst of *Cryptosporidium* existing in the environmental sample.

The invention will be further described in the following Examples but the description explains the invention further in detail and does not limit the scope of the invention.

Example 1

Detection of *Cryptosporidium* Oocyst Using UCST-Type Thermo-Responsive Magnetic Nanoparticles (i) Preparation of Standard Solution of *Cryptosporidium* Oocyst A 500 μl portion of a commercially available standard reagent of *Cryptosporidium parvum* oocyst (Waterborne™, Inc., $1.25\times10^6$/ml) was placed in a 1.5 ml tube, followed by centrifugation (10000 rpm) at room temperature for 5 minutes. After removal of the supernatant under suction, 0.5 ml of TBST buffer (20 mM Tris-HCl, 150 mM NaCl, 0.05% by mass Tween 20, pH 7.5) was added to the tube and the whole was subjected to vortex stirring. Furthermore, a commercially available immunofluorescent labeling reagent FITC-Anti-*Cryptosporidium* IgM (mAb) (Waterborne™, Inc., A400FLR-20X) was added in an amount which is 1/2000 of the liquid volume, followed by a reaction at room temperature for 10 minutes. Thereafter, 2 μl (KPL 0.5 ug/μl) of a commercially available biotinylated antimouse anti-IgM secondary antibody (IgG), followed by a reaction at room temperature for 10 minutes. Then, after 5 μl (10 mg/ml) of avidin was added thereto and the whole was allowed to stand at room temperature for 10 minutes, centrifugation (10000 rpm at room temperature) was conducted for 5 minutes and the supernatant was removed. Then, 0.5 ml of TBST buffer was added and unreacted FITC and anti-*Cryptosporidium* primary antibody, anti-IgM secondary antibody, and avidin were removed. A complex, named *Cryptosporidium* oocyst/anti*Cryptosporidium* oocyst fluorescent antibody/antifluorescent antibody biotinylated antibody/avidin was obtained, which was labeled with fluorescence and was bound to a biotinylated antibody through a fluorescent antibody and to avidin through biotin.

(ii) Separation of *Cryptosporidium* Oocyst

To 500 μl of an aqueous solution of *Cryptosporidium* oocyst/anti*Cryptosporidium* oocyst fluorescent antibody/antifluorescent antibody biotinylated antibody/avidin prepared by the above operations was added 50 μl of 1% by mass UCST-type biotinylated thermo-responsive magnetic nanoparticles. After standing at 42° C. for 2 minutes, a test tube was set on a magnet stand and was immersed and cooled in an ice bath at 0° C. for 5 minutes to conduct magnetic recovery of *Cryptosporidium* oocysts.

After magnetic separation, the supernatant was removed under suction by means of a pipette, 0.5 ml of TBST buffer was again added, and the UCST-type thermo-responsive magnetic nanoparticles were again dispersed at room temperature. After standing for 2 minutes, the UCST-type thermo-responsive magnetic nanoparticles dispersed were again aggregated by re-immersion into an ice bath and magnetic recovery of the UCST-type thermo-responsive magnetic nanoparticles by a magnet was conducted. The operations were further repeated twice and finally, 50 μl of TBST buffer was added to the aggregate of the UCST-type thermo-responsive magnetic nanoparticles from which washing liquid had been removed. The UCST-type thermo-responsive magnetic nanoparticles were again suspended with a pipette to prepare a sample for analyte.

(iii) Detection of *Cryptosporidium* Oocyst

A 2 μl portion of the sample for analyst thus prepared was dropped on a glass slide for observation without eluting the *Cryptosporidium* oocysts from UCST-type thermo-responsive magnetic nanoparticles, to form a preparation for observation.

Figure 2:
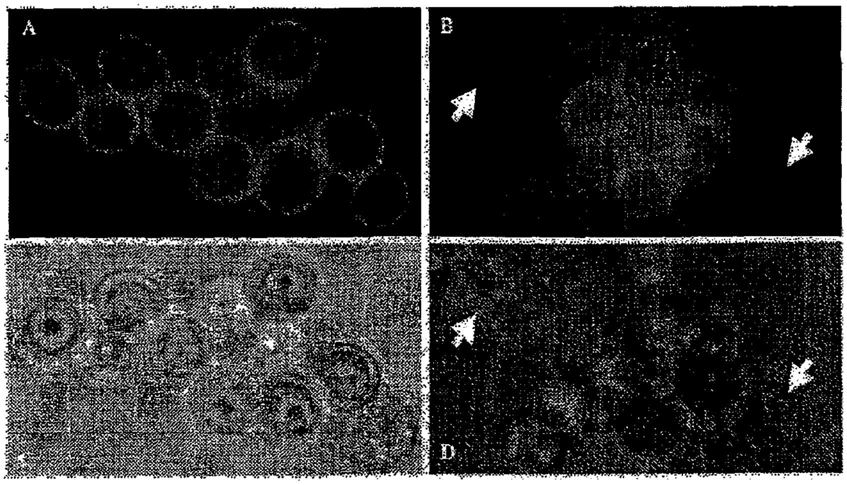
FIG. 2A is an immunological fluorescent microscopic photograph of *Cryptosporidium* oocysts separated with UCST-type heat responsive magnetic nanoparticles and FIG. 2B is an immunological fluorescent microscopic photograph of *Cryptosporidium* oocysts in an aggregated state separated with UCST-type heat responsive magnetic nanoparticles.
FIG. 2C and FIG. 2D are bright-field microscopic photographs of FIG. 2A and FIG. 2B, respectively.

As a result of observation of the above preparation, *Cryptosporidium* oocysts were efficiently detected as shown in FIG. 2.

Namely, FIG. 2A is an immunological fluorescent microscopic photograph of *Cryptosporidium* oocysts separated with the UCST-type thermo-responsive magnetic nanoparticles and FIG. 2C is a bright-field microscopic photograph thereof. In FIG. 2A, a fluorescent image of the UCST-type thermo-responsive magnetic nanoparticles is not observed and thus it is found that an efficient observation image is obtained without dissociation from the magnetic nanoparticles. Moreover, FIG. 2B is an immunological fluorescent microscopic photograph of *Cryptosporidium* oocysts in an aggregated state separated with the UCST-type thermo-responsive magnetic nanoparticles. The arrow part in FIG. 2B is an aggregate part of the UCST-type thermo-responsive magnetic nanoparticles but no fluorescent image is observed. The fact that fluorescence is not observed even in the aggregated state clearly indicates that it does not inhibit observation of the above thermo-responsive magnetic nanoparticles. FIG. 2D is a bright-field microscopic photograph of FIG. 2B and the arrow part in FIG. 2D is an aggregate of the UCST-type thermo-responsive magnetic nanoparticles.

Thus, since no UCST-type thermo-responsive magnetic nanoparticles were observed in the observed fluorescent image of the *Cryptosporidium* oocysts, it becomes apparent that separation of the UCST-type thermo-responsive magnetic nanoparticles from *Cryptosporidium* oocysts was not necessary after magnetic separation.

Furthermore, the supernatant after magnetic recovery was centrifuged (room temperature, 10000 rpm, 5 min) and recovery of unrecovered *Cryptosporidium* oocysts was attempted. After centrifugation, the supernatant was gently sucked and discarded, 50 μl of a fresh TBST buffer solution was added to the tube, and fluorescent detection of the oocyst was conducted but fluorescent *Cryptosporidium* oocyst was not observed in the supernatant. From the result, it was confirmed that *Cryptosporidium* oocysts were recovered from the analyte at an efficiency of almost 100%.

Comparative Example 1

A separation/detection test of *Cryptosporidium* by conventional micron-size magnetic beads was attempted.

(i) Observation of Micron-Size Magnetic Particles (Hereinafter also Referred to as Magnetic Beads) on a Fluorescent Microscope Before the separation test of *Cryptosporidium* oocysts, observation of a commercially available micron-size magnetic beads on a fluorescent microscope was conducted.

FIG. 3A is a bright-field microscopic photograph of commercially available magnetic beads and FIG. 3B is a fluorescent microscopic photograph of FIG. 3A. The color tone of fluorescence is not discriminated from fluorescent *Cryptosporidium* oocysts stained with FITC and also they extremely resemble each other in size. From this result, it was indicated that observation on a fluorescent microscope was difficult without elution of *Cryptosporidium* oocysts from the magnetic beads after recovery of *Cryptosporidium* oocysts.

(ii) Detection of *Cryptosporidium* Oocysts with *Cryptosporidium* Oocyst-Detecting Kit Using Conventional Micron-Size Magnetic Beads A 500 μl portion of a commercially available standard reagent of *Cryptosporidium parvum* oocyst (Waterborne™, Inc., $1.25\times10^6$/ml) was placed in a 1.5 ml tube, followed by centrifugation (10000 rpm) at room temperature for 5 minutes. After removal of the supernatant under suction, 0.5 ml of TBST buffer (20 mM Tris-HCl, 150 mM NaCl, 0.05% by mass Tween 20, pH 7.5) was added to the tube and the whole was subjected to vortex stirring. Then, 5 μl of DYNABEADS Anti-*Cryptosporidium* (VERITAS) was added, followed by gentle shaking for 1 hour. After shaking, a test tube was set on a magnet stand, the magnetic beads were collected and the supernatant was discarded. The test tube was removed from the magnet stand and 500 μl of TBST buffer was again added thereto, followed by gentle stirring for 30 minutes. Then, the test tube was set on the magnet stand, the immunological magnetic beads were collected, and the supernatant was discarded. The operations were further repeated twice and the beads were suspended in 50 μl of TBST buffer to prepare a sample for microscopic inspection.

FIG. 3C is a bright-field microscopic photograph and FIG. 3D is a fluorescent microscopic photograph of FIG. 3C. As shown by arrows in FIG. 3C and FIG. 3D, both of *Cryptosporidium* oocysts and the magnetic beads were observed on the bright-field microscopic photograph whereas only the magnetic beads were observed and *Cryptosporidium* oocyst were not observed on the fluorescent microscopic photograph. Those shown by arrows are *Cryptosporidium* oocysts separated by the commercially available magnetic beads but since they are not labeled with immunofluorescence, *Cryptosporidium* oocysts are not observed on a fluorescent microscope and thus commercially available magnetic beads are only observed.

Figure 3:
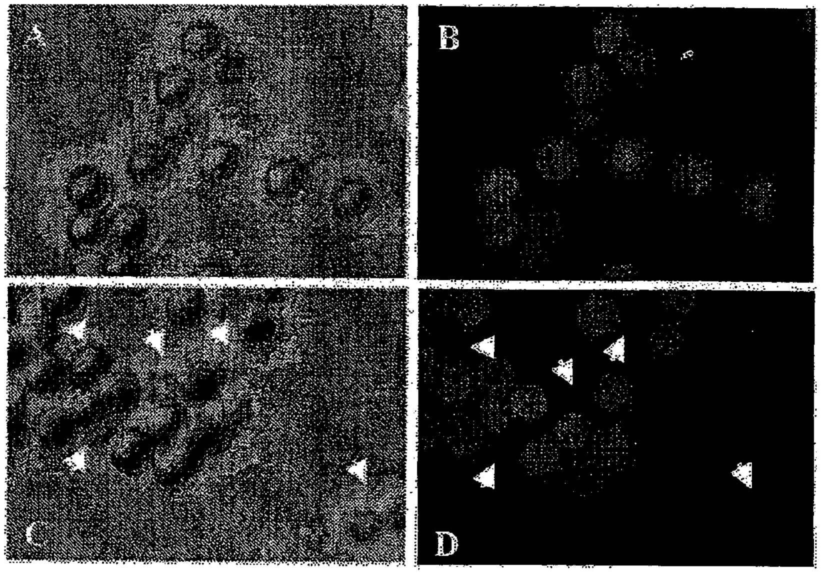
FIG. 3A and FIG. 3C are bright-field microscopic photographs of commercially available magnetic beads and FIG. 3B and FIG. 3D are fluorescent microscopic photographs of FIG. 3A and FIG. 3C, respectively.

Moreover, the magnetic particles and *Cryptosporidium* oocysts extremely resembled each other in both of size and shape as apparent from the bright-field and dark-field (fluorescent image) microscopic photographs in FIG. 3, it was confirmed that detection of *Cryptosporidium* oocysts on a fluorescent microscope was extremely difficult without elution operation of *Cryptosporidium* oocysts from the magnetic beads.

Example 2

Comparison of Separation Efficiency Between UCST-Type Thermo-Responsive Magnetic Nanoparticles and Conventional Micron-Size Magnetic Beads (i) Preparation of Sample After 1.68×10, 1.68×$10^2$, 1.68×$10^3$ or 1.68×$10^4$ oocysts of a commercially available standard reagent of *Cryptosporidium parvum* oocysts (Waterborne™, Inc., 1.25×$10^6$/ml) in 500 μl of TBST buffer was added to a tube, a *Cryptosporidium* oocyst/anti*Cryptosporidium* oocyst fluorescent antibody/antifluorescent antibody biotinylated antibody/avidin complex was formed according to Example 1. Thereafter, in accordance with Example 1, the above complex was reacted with biotinylated UCST-type thermo-responsive magnetic nanoparticles to separate *Cryptosporidium* oocysts. A finally recovered substance was suspended into 50 μl of a TBST buffer solution and the number of *Cryptosporidium* oocysts recovered was investigated on each sample.

(ii) Detection of *Cryptosporidium* Oocysts

In all the four samples, the equal number of oocysts to the number of the oocysts added in 500 μl of the TBST buffer was counted.

Moreover, the supernatant after magnetic recovery was further centrifuged (room temperature, 10000 rpm, 5 min) and separation of *Cryptosporidium* oocyst which had not been recovered was tried but the presence was not confirmed.

Comparative Example 2

An experiment similar to Example 2 was attempted using a commercially available *Cryptosporidium* oocyst-detecting kit. After 1.68×10, 1.68×$10^2$, 1.68×$10^3$ or 1.68×$10^4$ oocysts of a commercially available standard reagent of *Cryptosporidium parvum* oocysts (Waterborne™, Inc., 1.25×$10^6$/ml) in 500 μl of TBST buffer was added to a test tube, 5 μl of DYNABEADS Anti-*Cryptosporidium* (VERITAS) was added. After gentle shaking for 1 hour, the test tube was set on a magnet stand and the immunological magnetic beads were recovered and the supernatant was discarded. The magnetic beads were washed by repeating the following operations: the test tube was removed from the magnet stand and 500 μl of TBST buffer was once again added thereto to disperse the magnetic beads, and further the magnetic stand was set to recover magnetic beads and a supernatant was discarded. Then, 50 μl of 0.1N hydrochloric acid was added to the recovered magnetic beads to dissociate *Cryptosporidium* oocysts from the magnetic beads. A 50 μl portion of the dissociated liquid was placed on a glass slide and neutralized by adding 5 μl of 1N sodium hydroxide. After air-drying of the neutralized solution, 50 μl of methanol was added and the whole was again air-dried. To the air-dried sample was added 50 μl of a commercially available immunofluorescent labeling reagent FITC-Anti-*Cryptosporidium* IgM (mAb) (Waterborne™, Inc., A400FLR-20X) diluted to 1/2000, thereby fluorescent staining was conducted. After staining, the fluorescent labeling antibody solution was removed and 50 μl of ion-exchanged water was further added and removed to wash the sample, which was air-dried to form a preparation for observation.

When the number of *Cryptosporidium* oocysts was investigated, fluorescent counting results were lower than the theoretical number of *Cryptosporidium* oocysts for all the four samples.

Furthermore, when hydrochloric acid was again added to the magnetic beads, which had been magnetically recovered and from which *Cryptosporidium* had been dissociated, and detection of *Cryptosporidium* oocysts was tried in a similar manner, fluorescent *Cryptosporidium* oocysts were confirmed from the magnetic beads of all the four samples. The results indicate that recovery of *Cryptosporidium* oocyst is not completed by one dissociation operation. The observed counted number lower than the theoretical one may be attributed to the low recovery ratio.

Example 3

Separation of *Cryptosporidium* Oocysts From a Mixed Liquid with Yeast Cells with UCST-Type Thermo-Responsive Magnetic Nanoparticles Fluorescent staining of *Cryptosporidium* oocysts was attempted in the presence of an excess amount of yeast cells (*Saccharomyces cerevisiae*). Into 500 μl of TBST buffer were mixed 1×$10^6$ yeast cells (see FIG. 4A, which is a bright-field microscope photograph of yeast cells before immunofluorescent labeling) and 3×$10^5$ *Cryptosporidium* oocysts (see FIG. 4B, which is a bright-field microscope photograph of oocysts before immunofluorescent labeling). Then, 50 μl of a commercially available immunofluorescent labeling reagent FITC-Anti-*Cryptosporidium* IgM (mAb) (Waterborne™, Inc., A400FLR-20X) diluted to 1/2000 was added, thereby fluorescent labeling was conducted. Centrifugation at room temperature for 1000 rpm for 5 minutes was conducted and then the precipitate was recovered and the supernatant was discarded. Further, TBST buffer was added and the whole was stirred, followed by centrifugation at room temperature for 1000 rpm for 5 minutes. After this operation was further repeated twice, the precipitate was dispersed into 50 μl of TBST buffer to prepare a sample for observation.

Figure 4:
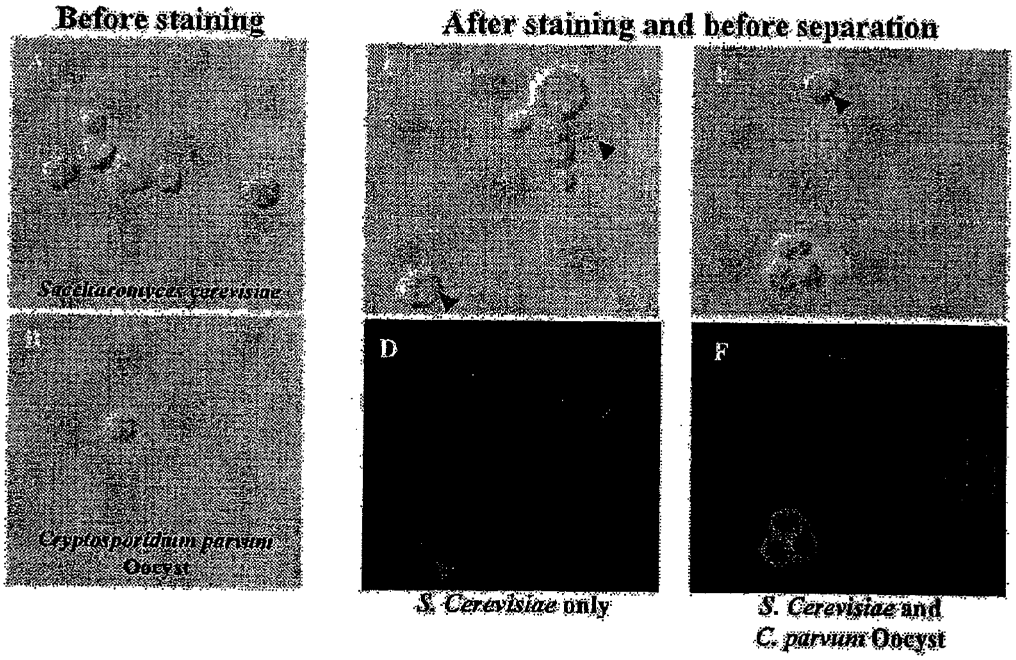
FIG. 4A and FIG. 4B are bright-field microscope photographs of yeast cells and oocysts before immunological fluorescent labeling.
FIG. 4C and FIG. 4D are a bright-field microscope photograph and a fluorescent microscopic photograph of the yeast cells after immunological fluorescent labeling, respectively.
FIG. 4E and FIG. 4F are a bright-field microscope photograph and a fluorescent microscopic photograph of an excess amount of the yeast cells and *Cryptosporidium* oocysts subjected to immunological fluorescent labeling after they are mixed, respectively.

As a result, as shown by arrows in FIG. 4C to FIG. 4F, in both of immunological fluorescent images of the yeast cells alone (see FIG. 4C and FIG. 4D; FIG. 4C is a bright-field microscope photograph and FIG. 4D is a fluorescent microscopic photograph of the yeast cells after immunofluorescent labeling) and the case where the yeast cells and *Cryptosporidium* oocysts were mixed (see FIG. 4E and FIG. 4F; images of an excess amount of the yeast and *Cryptosporidium* oocyst subjected to immunofluorescent labeling after they are mixed; FIG. 4E is a bright-field microscope photograph and FIG. 4F is a fluorescent microscopic photograph thereof), the arrowed yeast cells were not confirmed on a fluorescent microscope and only the *Cryptosporidium* oocysts were observed (see FIG. 4F).

Moreover, separation of *Cryptosporidium* oocysts from an analyte (liquid) containing the yeast cells and *Cryptosporidium* oocysts in the above concentrations was conducted in accordance with Example 1.

Figure 5:
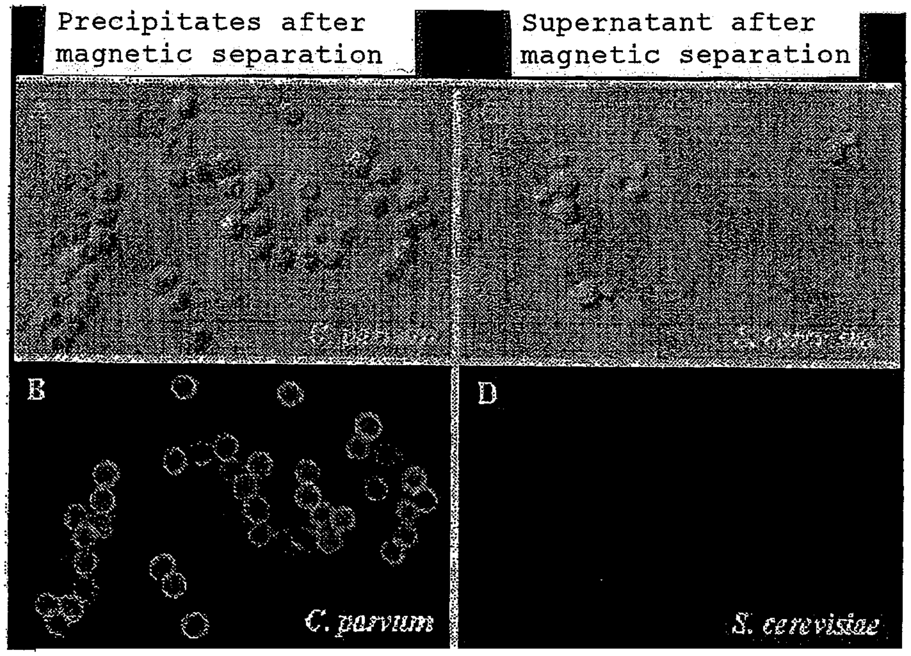
FIG. 5A is a bright-field microscopic photograph of magnetic nanoparticle aggregates separated with UCST-type thermo-responsive magnetic nanoparticles and FIG. 5B is a fluorescent microscopic photograph thereof.
FIG. 5C is a bright-field microscopic photograph of remaining supernatant after separated with UCST-type thermo-responsive magnetic nanoparticles and FIG. 5D is a fluorescent microscopic photograph thereof.

As a result, only *Cryptosporidium* oocysts were detected from magnetic aggregate of UCST-type thermo-responsive magnetic nanoparticles but no yeast cells were detected (see FIG. 5A and FIG. 5B; FIG. 5A is a bright-field microscopic photograph of magnetic nanoparticle aggregates separated with UCST-type thermo-responsive magnetic nanoparticles and FIG. 5B is a fluorescent microscopic photograph thereof).

On the other hand, in the supernatant after magnetic recovery, only the yeast cells were detected but no *Cryptosporidium* oocysts were detected (see FIG. 5C and FIG. 5D; FIG. 5C is a bright-field microscopic photograph of remaining supernatant after separated with UCST-type thermo-responsive magnetic nanoparticles and FIG. 5D is a fluorescent microscopic photograph thereof).

The invention claimed is:

1. A method for measuring *Cryptosporidium parvum* oocysts in water, which comprises:

adding magnetic fine particles of 150 to 500 nm particle diameter, which have an antioocyst antibody for specifically recognizing *Cryptosporidium parvum* oocysts immobilized thereto, to an aqueous analyte containing *Cryptosporidium parvum* oocysts to form complexes of the *Cryptosporidium parvum* oocysts with the magnetic fine particles through the antioocyst antibody, wherein the magnetic fine particles are magnetic fine particles having stimuli-responsive upper critical solution temperature (UCST) polymers immobilized thereto;

recovering the thus formed *Cryptosporidium parvum* oocyst/antioocyst antibody/magnetic fine particle complexes by a magnetic separation; and counting the number of *Cryptosporidium parvum* oocysts.

2. The method for measuring protozoan oocysts according to claim 1, wherein the *Cryptosporidium parvum* oocyst/antioocyst antibody/magnetic fine particle complexes are *Cryptosporidium parvum* oocyst/antioocyst antibody/magnetic fine particle complexes formed by adding magnetic fine particles having the antioocyst antibody immobilized thereto to the analyte.

3. The method for measuring protozoan oocysts according to claim 1, wherein the antioocyst antibody has a binding factor component specifically recognizing the antioocyst antibody bound thereto (hereinafter referred to as "antioocyst antibody-binding factor component").

4. The method for measuring protozoan oocysts according to claim 3, wherein the oocyst/antioocyst antibody/magnetic fine particle complexes are oocyst/antioocyst antibody/antioocyst antibody-binding factor component/magnetic fine particle complexes, which are formed by adding antibodies against oocyst to an analyte to form oocyst/antioocyst antibody complexes, and subsequently adding magnetic fine particles having the antioocyst antibody-binding factor component against the antibody immobilized thereto.

5. The method for measuring protozoan oocysts according to claim 1, further comprising labeling the magnetic fine particles before adding the magnetic fine particles.

6. The method for measuring protozoan oocysts according to claim 1, further comprising labeling oocyst/antioocyst antibody/magnetic fine particle complexes after adding the magnetic fine particles.

7. The method for measuring protozoan oocysts according to claim 6, wherein the labeling is fluorescent labeling.

8. The method for measuring protozoan oocysts according to claim 6, wherein the labeling is fluorescent labeling.

* * * * *